(12) United States Patent
Starks

(10) Patent No.: US 9,149,036 B1
(45) Date of Patent: Oct. 6, 2015

(54) METHOD FOR APPLYING A PERSISTENT ANTIMICROBIAL FILM

(71) Applicant: Lloyd Starks, Chattanooga, TN (US)

(72) Inventor: Lloyd Starks, Chattanooga, TN (US)

( * ) Notice: Subject to any disclaimer, the term of this patent is extended or adjusted under 35 U.S.C. 154(b) by 0 days.

(21) Appl. No.: 14/195,697

(22) Filed: Mar. 3, 2014

Related U.S. Application Data

(60) Provisional application No. 61/832,016, filed on Jun. 6, 2013.

(51) Int. Cl.
| | | |
|---|---|---|
| *A61K 31/715* | (2006.01) | |
| *A61K 31/722* | (2006.01) | |
| *B05D 7/00* | (2006.01) | |
| *A01N 43/16* | (2006.01) | |

(52) U.S. Cl.
CPC ..................................... *A01N 43/16* (2013.01)

(58) Field of Classification Search
CPC ........ B32B 27/04; B32B 27/02; B32B 27/12; B05D 7/00; A61K 31/715; A61K 31/722
USPC ................. 427/2.1, 248.1, 255.394
See application file for complete search history.

(56) References Cited

U.S. PATENT DOCUMENTS

| | | | | |
|---|---|---|---|---|
| 6,004,667 A | * | 12/1999 | Sakurada et al. | 428/323 |
| 6,197,322 B1 | * | 3/2001 | Dutkiewicz et al. | 424/412 |
| 8,226,962 B2 | | 7/2012 | Xin et al. | |
| 2001/0055622 A1 | * | 12/2001 | Burrell et al. | 424/600 |
| 2003/0031872 A1 | * | 2/2003 | Arps et al. | 428/408 |
| 2004/0135967 A1 | * | 7/2004 | Carney et al. | 351/159 |
| 2005/0008676 A1 | * | 1/2005 | Qiu et al. | 424/429 |
| 2005/0075027 A1 | * | 4/2005 | Etchells et al. | 442/205 |
| 2005/0118239 A1 | * | 6/2005 | Sabesan | 424/443 |
| 2006/0062850 A1 | | 3/2006 | Chen et al. | |
| 2006/0228966 A1 | * | 10/2006 | Gleason et al. | 442/123 |
| 2007/0254006 A1 | * | 11/2007 | Loose et al. | 424/423 |
| 2009/0035342 A1 | * | 2/2009 | Karandikar et al. | 424/411 |
| 2009/0324536 A1 | * | 12/2009 | Sun et al. | 424/78.23 |
| 2010/0285084 A1 | * | 11/2010 | Yang et al. | 424/423 |
| 2011/0250626 A1 | * | 10/2011 | Williams et al. | 435/18 |
| 2012/0276278 A1 | * | 11/2012 | Qiu et al. | 427/2.1 |

OTHER PUBLICATIONS

Martin, T.P., et al., "Initiated chemical vapor deposition of antimicrobial polymer coatings." Biomaterials 28 (2007) 909-915.*
Torres-Giner, S., et al., "Development of Active Antimicrobial Fiber Based Chitosan Polysaccharide Nanostructures using Electrospinning". Eng. Life. Sci. 2008, 8, No. 3, 303-314.*
Goy, Rejane C, et al., "A Review of the Antimicrobial Activity of Chitosan". Polimeros: Ciencia e Tecnologia, vol. 19, No. 3, pp. 241-247, 2009.*
Zhao, Li-Ming, et al., "Preparation and Application of Chitosan Nanoparticles and Nanofibers". Brazilian Journal of Chemical Engineering. vol. 28, No. 03, pp. 353-362, Jul.-Sep. 2011.*
Kubacka, Anna, et al., "Understanding the antimicrobial mechanism of TiO2-based nanocomposite films in a pathogenic bacterium". Scientific Reports 4:4134, Feb. 19, 2014, pp. 1-9.*
Duan, J., et al., "Storability of Antimicrobial Chitosan-Lysozyme Composite Coating and Film-Forming Solutions." Journal of Food Science, vol. 73, Nr.6, 2008, M321-M329.*
Tripathi, Shipra, et al., "Chitosan based antimicrobial films for food packaging applications". e-Polymers 2008, No. 093, pp. 1-7.*
Coma, Veronique, "Polysaccharide-based Biomaterials with Antimicrobial and Antioxidant Properties". Polimeros, vol. 23, N. 3, pp. 287-297, 2013.*
Sanchez-Gonzalez, Laura, et al., "Antimicrobial activity of polysaccharide films containing essential oils". Food Control 22 (2011) 1302-1310.*
Coma, V, et al., "Edible Antimicrobial Films Based on Chitosan Matrix". Food Microbiology and Safety, pp. 1-8. No other reference information available.*

* cited by examiner

*Primary Examiner* — Bret Chen
(74) *Attorney, Agent, or Firm* — Gerald M. Walsh; Leo Law Firm, LLC

(57) ABSTRACT

A method for sanitizing and disinfecting a surface using an aqueous solution of chitosan. The aqueous solution is heated to convert the aqueous solution to a steam vapor containing chitosan. The surface is treated with the steam, thereby disinfecting the surface and simultaneously depositing the chitosan from the steam onto the surface. The steam will also penetrate porous surfaces. An antimicrobial film of chitosan is thereby formed on the surface. The steam vapor sterilizes the surface and the chitosan film inhibits growth of bacteria and other microbes on the surface for several months. The steam containing the chitosan can be generated from an aqueous solution of chitosan heated in standard commercial and home-use steam generators. This chitosan vapor steam treatment of surfaces can be used on any hard surface or soft surface.

8 Claims, No Drawings

METHOD FOR APPLYING A PERSISTENT ANTIMICROBIAL FILM

CROSS-REFERENCE TO RELATED APPLICATIONS

This application claims priority of U.S. Provisional Application Ser. No. 61/832,016 filed Jun. 6, 2013, the disclosure of which is incorporated herein by reference.

FIELD OF THE INVENTION

The present invention relates to methods of disinfecting surfaces and, more particularly, to disinfecting surfaces with steam and with chitosan contained in the steam, wherein the chitosan forms a durable antimicrobial film on the surface.

BACKGROUND OF THE INVENTION

There is need to disinfect surfaces and materials within buildings and other enclosures, such as locker rooms, clubhouses, gymnasiums, equipment related to athletic activities, health care facilities, and vehicles for transportation for land, sea, and air. It is known to use steam for disinfecting surfaces. Portable steam generators are commercially available which typically work with a "wand" that allows manual application of steam directly to surfaces of floors, walls, ceilings, fixtures, furniture, equipment, and the like. Such application of steam sterilizes these surfaces but does not provide an on-going antimicrobial protection of these surfaces.

Chitosan possesses good antibacterial properties against various bacteria and fungi because of its polycationic nature. Chitosan is obtained from the shells of crabs, shrimps and other crustaceans. It is a non-toxic, biodegradable and biocompatible natural polymer, and has long been used as a biopolymer and natural material in pharmaceutical, medical, papermaking and food processing industries. Chitosan is a basic polysaccharide obtained by deacetylation of the chitin which is present in the carapace of these crustaceans. However, because of strong hydrogen bonds, chitosan itself is hardly soluble in a solvent other than an acidic aqueous solution and, even if it is made into an aqueous solution, the viscosity of the solution can become high whereby its handling is difficult. In addition, Chitosan has strong water-absorption ability due to the presence of many hydrophilic polar groups. In order to overcome these problems chitosan has been incorporated into polymeric core-shell particles dispersed in water (see U.S. Pat. No. 8,226,962). This methodology is relatively complex and appears useful only for textiles and not for all surfaces.

What is needed is an aqueous solution of chitosan or related substances that overcomes the problems of viscosity, high acidity, and water absorption and which will provide sustained antimicrobial protection to all surfaces by a simple method of application.

SUMMARY OF THE INVENTION

This invention provides a method for disinfecting a surface using antimicrobial nitrogen-containing polysaccharides in vapor. A liquid solution of an antimicrobial nitrogen-containing polysaccharide is heated to convert the liquid solution to a vapor. The surface is then exposed to the vapor, thereby disinfecting the surface and depositing the antimicrobial nitrogen containing polysaccharide from the vapor onto the surface, thereby forming an antimicrobial film of the nitrogen containing polysaccharide on the surface. The antimicrobial nitrogen-containing polysaccharide is, preferably, a chitin derivative and the chitin derivative is, preferably, chitosan. The chitosan may be in the form of carboxymethylated chitosan. If a chitin derivative, such as chitosan, is used the liquid solution is water and the vapor is steam. The steam is, preferably, dry vapor steam.

This invention also provides an antimicrobial composition containing an antimicrobial nitrogen-containing polysaccharide in a vapor. The antimicrobial nitrogen-containing polysaccharide may be a chitin derivative, preferably chitosan or carboxymethylated chitosan. If the antimicrobial nitrogen-containing polysaccharide is chitosan then the vapor is steam, preferably dry vapor steam.

An advantage of the present invention is the ability to deliver the antimicrobial agent chitosan in steam vapor to a surface wherein the steam vapor sterilizes the surface and the chitosan simultaneously forms a more durable antimicrobial film on the surface, compared to applications at ambient/room temperature.

Another advantage is that the sterilization and formation of the durable antimicrobial chitosan film on the surface requires only 3 to 10 seconds of exposure of the surface to the steam.

Another advantage is that the durable antimicrobial chitosan film on the surface will inhibit growth of bacteria and other microbes on the surface for several months.

Another advantage is that the steam containing the chitosan can be generated from an aqueous solution of chitosan heated in standard commercial and home-use steam generators.

Another advantage is that this chitosan vapor steam treatment of surfaces can be used on any hard surface or soft surface, including textiles, fabrics, garments, clothes, and shoes, wherein the steam penetrates porous surfaces.

Another advantage is a dry vapor steam process which accomplishes pre-cleaning, disinfecting/sanitization, and persistent antimicrobial film deposition on a surface in a single step.

DETAILED DESCRIPTION OF THE INVENTION

While the following description details the preferred embodiments of the present invention, it is to be understood that the invention is not limited in its application to the details of the method described herein, since the invention is capable of other embodiments and of being practiced in various ways.

Chitosan inhibits the growth of a wide variety of bacteria and fungi. Moreover, chitosan has several advantages over other types of disinfectants, that is, it possesses a higher antibacterial activity, a broader spectra of activity, a higher killing rate, and lower toxicity toward mammalian cells. Several mechanisms are proposed for the antimicrobial activity by chitosan. In one mechanism, the polycationic nature of chitosan interferes with the negatively charged residues of macromolecules at the cell surface. Chitosan interacts with the membrane of the cell to alter cell permeability. In another mechanism the binding of chitosan with DNA inhibits RNA synthesis.

Chitosan is a linear polysaccharide composed of randomly distributed β-(1-4)-linked D-glucosamine (deacetylated unit) and N-acetyl-D-glucosamine (acetylated unit). Chitosan is produced commercially by deacetylation of chitin, which is the structural element in the exoskeleton of crustaceans (such as crabs and shrimp). The degree of deacetylation in commercial chitosans ranges from 60 to 100%. On average, the molecular weight of commercially produced chitosan is between 3800 and 20,000 Daltons. A common method for the synthesis of chitosan is the deacetylation of chitin using sodium hydroxide in excess as a reagent and water as a solvent. This reaction pathway, when allowed to go to complete deacetylation yields up to 98% chitosan.

Chitosan

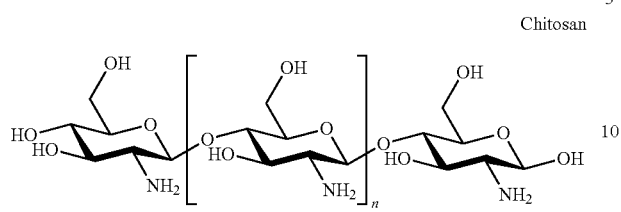

The present invention provides a method of using a solution of an antimicrobial nitrogen-containing polysaccharide dissolved in an aqueous medium to sanitize and disinfect a surface and to deposit the antimicrobial nitrogen-containing polysaccharide on the surface to provide sustained antimicrobial protection of the surface. Preferably, the nitrogen-containing polysaccharide is chitin or a chitin derivative such as chitosan or carboxymethylated chitosan. The nitrogen-containing polysaccharide is dispersed in water to form an aqueous solution. In a preferred embodiment, a chitosan solution is obtained by diluting a 5.75% solution of a chitosan concentrate in deionized water, at room temperature at a 1:21 ratio by volume. The final concentration of the diluted chitosan in the aqueous medium can range from 0.1 to 0.6%, preferably 0.27% by volume (the chitosan treatment solution). This chitosan treatment solution is used for sterilization of and vapor deposition onto surfaces. The chitosan is, preferably, at least a partially N-deacetylated derivative of chitin. Chitosans of various molecular weights and degrees of N-deacetylation are available commercially. In the present invention, the molecular weight of chitosan is higher than 10,000 and the degree of N-deacetylation is in the range of 10% to 100%. It is desirable to have a medium molecular weight of chitosan (50,000 to 100,000) with a degree of N-deacetylation higher than 70%. Chitosan can be obtained from Chem-Tex Laboratories, Concord, N.C.

The chitosan treatment solution is used in the form of a vapor to sterilize a surface and simultaneously coat the surface with a dry film of chitosan. If the chitosan treatment solution is an aqueous solution then the vapor will be steam. Any kind of steam generating system can be used to convert the chitosan aqueous treatment solution to steam. However, dry vapor steam is preferred wherein the steam is at a temperature of at least 275° F., preferably 275° F. to 310° F. For example, Advanced Vapor Technologies, LLC of Everett, Wash. provides a variety of commercial and residential dry vapor steam generating systems. Another source is AmeriVap Systems, Dawsonville, Ga. Dry vapor steam is steam having a temperature ranging from 240° F. to 310° F., a water moisture content of 4% to 6%, and pressure up to 140 PSI.

In order to sanitize and disinfect a surface and apply a film of chitosan to the surface using the chitosan treatment solution, the chitosan treatment solution is placed in the dry vapor steam generating system. The chitosan treatment solution is heated in the dry vapor steam generating system to produce vapor steam at a temperature of at least 275° F. The steam is applied to the surface for 1 to 20 seconds, preferably 5 to 10 seconds, at an angle of preferably approximately 90°, and at a distance of 1 to 20 inches, preferably 6-10 inches. After application of the steam the surface has a thin film of chitosan deposited thereon. A composition of steam and chitosan is formed in the generation of dry vapor steam from the chitosan treatment solution. No chitosan treatment solution in its liquid form is applied to the surface in this process. The steam sterilizes/disinfects the surface. The chitosan in the steam vapor deposits on the surface forming a water resistant antimicrobial durable film of chitosan. The chitosan film inhibits growth of microbes on the surface for a sustained period of time. The method is referred to as the chitosan vapor steam treatment or the chitosan dry vapor steam treatment.

Example 1

Studies were performed to demonstrate the initial sterilization of the dry vapor steam generated from the chitosan treatment solution on glass slides (carriers) using a surface time-kill procedure of a test microorganism. The glass slides were 1"×3". These glass slides were also tested after the dry vapor steam treatment by re-inoculation with the test organism. The inoculum dwelled on the slides for several contact times to determine the amount of time necessary to reduce colony forming units (CFU) by at least 99.9%.

The surfaces of sterile glass carriers were inoculated with 0.020 ml of an overnight culture of *S. aureus* ATCC 6538 and dried in ambient conditions for 30 minutes before treatment with dry vapor steam generated from the chitosan treatment solution. The chitosan treatment solution was created by mixing 1 part of a 5.75±10% commercial aqueous chitosan solution with 21 parts of water. The resulting aqueous chitosan solution was poured into a commercial dry vapor steam cleaning unit and allowed to equilibrate for about 15 minutes. The surfaces of the inoculated glass carriers were exposed to dry vapor steam at approximately a 45° angle and 8 inches from the surfaces of the glass carriers for 10 seconds. A portion of these treated glass carriers were harvested in 10 mL D/E neutralization buffer 30 seconds after the end of steam treatment. These glass carriers along with untreated controls were enumerated using standard plating techniques. Remaining glass carriers where then inoculated with sterile 200 µL water containing ~8.0×10$^5$ CFU of *S. aureus* ATCC 6538. These glass carriers were incubated under high humidity (>85% RH) for 2, 6, and 24 hours. Upon reaching each contact time, treated and control glass carriers were harvested and enumerated as mentioned above.

Results of these studies are shown in Table 1. Treatment at time zero with the dry vapor steam containing chitosan reduced CFU on the treated carriers by greater than 99.9% compared to the controls. These results indicate that the dry vapor steam containing chitosan sterilizes/disinfects the surface of the glass carriers. At 2, 6, and 24 hours after re-inoculation of the surfaces of the glass carriers, there was still a reduction in CFU greater than 99.9% compared to controls. These results indicate that the dry vapor steam treatment produced a sustained antimicrobial effect on the surfaces of the glass carriers. This sustained antimicrobial effect is due to the presence of a water-resistant film of chitosan deposited on the surface of the glass carriers by the chitosan dry vapor steam treatment.

Example 2

Studies were performed to determine if the chitosan film deposited on the surface of glass and cotton carriers by the chitosan dry vapor steam treatment retained antimicrobial effects against a test microorganism for a period of days and weeks following the treatment.

Sterile glass (1"×3") and cotton carriers (4.8 cm cotton discs) were treated with *S. aureus* ATCC 6538 as described in Example 1. The chitosan dry vapor steam treatment was the same as described in Example 1 except that the angle of deposition of dry vapor steam was about 90°. The first inoculation was 50 μL of water containing about $1.0 \times 10^5$ CFU. All subsequent inoculations were similar and occurred on days 1, 2, 3, 7, 14, and 21 for a total of 7 bacterial challenges. The glass carriers and cotton carriers remained in ambient conditions for the remaining persistence times. The contact time chosen for each persistence inoculation was 2 hours. Upon reaching this contact time, treated and control glass carriers and cotton carriers were harvested and enumerated using standard plating techniques.

Results of these studies are shown in Table 2. Two hours after inoculation of the glass and cotton carriers, on days 1, 2, and 3 and weeks 1, 2, and 3 following the chitosan dry vapor steam treatment, there was a reduction in CFU greater than 99.9% on the treated carriers compared to controls. These results indicate that the chitosan dry vapor steam treatment produced a sustained antimicrobial effect on the surfaces of the glass and cotton carriers up to 3 weeks. This sustained antimicrobial effect is due to the presence of a water-resistant film of chitosan deposited on the surface of the glass and cotton carriers by the chitosan dry vapor steam treatment.

Example 3

Studies were performed to determine if the chitosan film deposited on the surface of glass and cotton carriers by the chitosan dry vapor steam treatment retained antimicrobial effects against a test microorganism for a period of months following the treatment.

Sterile glass (1"×3") and cotton carriers (4.8 cm cotton discs) were treated with *S. aureus* ATCC 33592 (MRSA) as described in Example 2. The chitosan dry vapor steam treatment was the same as described in Example 2 except that the steam was applied to the glass and cotton surfaces for 5 seconds. The treated and control glass and cotton carriers were then aged for 4 months in ambient laboratory conditions. An aliquot of an overnight culture was added to 10 ml sterile water to create the test inoculum (ATCC 33592). The glass and cotton carriers were inoculated with 50 μl of the inoculum for a target of $\sim 1.0 \times 10^5$ CFU/Carrier. The inoculated treated and untreated carriers were then incubated for 10 minutes at room temperature. Upon reaching each contact time, carriers were harvested in 10 mL D/E neutralization broth and enumerated using conventional dilution plating techniques. CFU reductions in the treated carriers were calculated using cell titer data for the control carriers after the contact time.

Results of these studies are shown in Table 3. Ten minutes after inoculation of the glass and cotton carriers, at 4 months following the chitosan dry vapor steam treatment, there was a reduction in CFU greater than 99.9% on the surfaces of the treated carriers compared to the controls. These results indicate that the chitosan dry vapor steam treatment produced a sustained antimicrobial effect on the surfaces of the glass and cotton carriers up to 4 months. This sustained antimicrobial effect is due to the presence of a water-resistant film of chitosan deposited on the surface of the glass and cotton carriers by the chitosan dry vapor steam treatment.

The chitosan dry vapor steam treatment can be applied to any hard or soft surface. A hard surface is one that resists compression such as, for example, the surfaces of floors, walls, ceilings, counter tops, doors, fixtures, equipment, and other solid objects. A soft surface is one that does not resist compression, for example, the surfaces of fibrous articles, woven articles, textiles, plastic foams, and the like. A soft surface may have air-laid or woven material. The present chitosan steam vapor composition and treatment method offers a unique, one-step bactericide, wherein the steam may be applied to a surface a first time to destroy bacteria, and then leave a chitosan film that can inhibit bacterial growth on an on-going basis.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the chitosan dry vapor steam treatment has many uses and applications. The surfaces in surgical rooms, athletic locker rooms, and military barracks may be sterilized/sanitized by the chitosan dry vapor steam treatment. The surfaces of the objects, devices, equipment, and countertops therein may also be sterilized/sanitized. The steam may be pressurized or unpressurized. The steam can be delivered through any kind of hose, wand, nozzle, and the like. Any type of steam generating device can be used to implement the chitosan dry vapor steam treatment, including, for example, the ordinary consumer clothes iron.

It will be understood that various changes in the details, materials, and arrangements of the parts which have been described above in order to explain the nature of this invention may be made by those skilled in the art without departing from the principle and scope of the invention as recited in the following claims.

TABLE 1

| Contact Time* | Sample | Replicate Number | CFU/Carrier | Average CFU/Carrier | Percent Reduction |
|---|---|---|---|---|---|
| Time Zero | Control | 1 | 2.25E+07 | 2.36E+07 | N/A |
| | | 2 | 2.46E+07 | | |
| | Treated | 1 | 2.00E+00 | 1.50E+00 | 99.999994% |
| | | 2 | 1.00E+00 | | |
| 2 hours | Control | 1 | 1.41E+07 | 1.37E+07 | N/A |
| | | 2 | 1.32E+07 | | |
| | Treated | 1 | 1.18E+02 | 6.00E+01 | 99.999560% |
| | | 2 | 2.00E+00 | | |
| 6 hours | Control | 1 | 9.30E+06 | 1.06E+07 | N/A |
| | | 2 | 1.18E+07 | | |
| | Treated | 1 | 2.00E+00 | 1.50E+00 | 99.999986% |
| | | 2 | 1.00E+00 | | |
| 24 hours | Control | 1 | 8.10E+07 | 8.20E+07 | N/A |
| | | 2 | 8.30E+07 | | |
| | Treated | 1 | 2.00E+00 | 4.00E+00 | 99.999995% |
| | | 2 | 6.00E+00 | | |

*Test microorganism *S. aureus* ATCC 6538

TABLE 2

| Contact Time* | Sample | Surface Type | Replicate Number | CFU/Carrier | Average CFU/Carrier | Percent Reduction |
|---|---|---|---|---|---|---|
| Time Zero | Control | glass | 1 | 1.00E+05 | 1.05E+05 | N/A |
| | | | 2 | 1.10E+05 | | |
| | | cotton | 1 | 1.70E+04 | 2.08E+04 | |
| | | | 2 | 2.45E+04 | | |

TABLE 2-continued

| Contact Time* | Sample | Surface Type | Replicate Number | CFU/Carrier | Average CFU/Carrier | Percent Reduction |
|---|---|---|---|---|---|---|
| 24 hours 2 challenges | Control | glass | 1 | 1.90E+05 | 1.98E+05 | |
| | | | 2 | 2.05E+05 | | |
| | | cotton | 1 | 2.25E+04 | 3.43E+04 | |
| | | | 2 | 4.60E+04 | | |
| | Treated | glass | 1 | <2.00E+00 | <2.00E+00 | >99.9990% |
| | | | 2 | <2.00E+00 | | |
| | | cotton | 1 | <2.00E+00 | <2.00E+00 | >99.994% |
| | | | 2 | <2.00E+00 | | |
| 48 hours 3 challenges | Control | glass | 1 | 1.80E+05 | 1.93E+05 | N/A |
| | | | 2 | 2.05E+05 | | |
| | | cotton | 1 | 8.45E+04 | 9.73E+04 | |
| | | | 2 | 1.10E+05 | | |
| | Treated | glass | 1 | <2.00E+00 | <2.00E+00 | >99.9990% |
| | | | 2 | <2.00E+00 | | |
| | | cotton | 1 | <2.00E+00 | <2.00E+00 | >99.998% |
| | | | 2 | <2.00E+00 | | |
| 72 hours 4 challenges | Control | glass | 1 | 2.00E+05 | 2.55E+05 | N/A |
| | | | 2 | 3.10E+05 | | |
| | | cotton | 1 | 2.45E+04 | 1.75E+04 | |
| | | | 2 | 1.05E+04 | | |
| | Treated | glass | 1 | <2.00E+00 | <2.00E+00 | >99.9992% |
| | | | 2 | 2.00E+00 | | |
| | | cotton | 1 | <2.00E+00 | <2.00E+00 | >99.989% |
| | | | 2 | <2.00E+00 | | |
| 1 week 5 challenges | Control | glass | 1 | 1.70E+05 | | N/A |
| | | cotton | 1 | 5.70E+04 | | |
| | Treated | glass | 1 | <2.00E+00 | | >99.9994% |
| | | cotton | 1 | <2.00E+00 | | >99.998% |
| 2 weeks 6 challenges | Control | glass | 1 | 3.00E+05 | | N/A |
| | | cotton | 1 | 7.00E+04 | | N/A |
| | Treated | glass | 1 | <2.00E+00 | | >99.9997% |
| | | cotton | 1 | <2.00E+00 | | >99.9986% |
| 3 weeks 7 challenges | Control | glass | 1 | 3.30E+05 | | N/A |
| | | cotton | 1 | 5.05E+04 | | |
| | Treated | glass | 1 | <2.00E+00 | | >99.9997% |
| | | cotton | 1 | <2.00E+00 | | >99.998% |

*Test microorganism *S. aureus* ATCC 6538

TABLE 3

| Sample | Contact Time* | Surface Type | Replicate Number | CFU/Carrier | Average CFU/Carrier | Log10 Reduction | Percent Reduction |
|---|---|---|---|---|---|---|---|
| Untreated (control) | Time-Zero | glass | 1 | 1.55E+05 | 1.33E+05 | N/A | |
| | | | 2 | 1.10E+05 | | | |
| | | cotton | 1 | 1.40E+05 | 1.30E+05 | | |
| | | | 2 | 1.20E+05 | | | |
| | 10 min | glass | 1 | 1.35E+05 | 1.25E+05 | | |
| | | | 2 | 1.15E+05 | | | |
| | | cotton | 1 | 7.30E+04 | 9.90E+04 | | |
| | | | 2 | 1.25E+05 | | | |
| Treated (Test) | 10 min | glass | 1 | <5.00E+00 | <5.00E+00 | >4.40 | >99.996% |
| | | | 2 | <5.00E+00 | | | |
| | | cotton | 1 | 1.00E+01 | <7.50E+00 | >4.12 | >99.992% |
| | | | 2 | <5.00E+00 | | | |

*Test microorganism *S. aureus* ATCC 33592 (MRSA); samples aged for 4 months.

I claim:

1. A method for sanitizing or disinfecting a surface and simultaneously forming an antimicrobial film on said surface, comprising:
   1) providing a liquid water solution of an antimicrobial nitrogen-containing polysaccharide;
   2) heating said liquid water solution to convert said liquid water solution to a water vapor;
   3) exposing said surface to said water vapor, thereby sanitizing or disinfecting said surface with heat; and
   4) simultaneously depositing said antimicrobial nitrogen containing polysaccharide from said water vapor onto said surface, thereby forming said antimicrobial film of said nitrogen containing polysaccharide on said surface.

2. The method of claim 1 wherein said antimicrobial nitrogen-containing polysaccharide is a chitin derivative or chitosan or carboxymethylated chitosan.

3. The method of claim 2 wherein said water vapor is steam or dry vapor steam.

4. A method for sanitizing or disinfecting a surface and simultaneously forming an antimicrobial film on said surface, comprising:
   1) providing a water solution of chitosan or carboxymethylated chitosan;

2) heating said water solution to convert said water solution to a water dry vapor steam;

3) exposing said surface to said water dry vapor steam, thereby sanitizing or disinfecting said surface with heat; and 4) simultaneously depositing said chitosan from said water dry vapor steam onto said surface, thereby forming an antimicrobial film of chitosan on said surface.

5. A method for sanitizing or disinfecting a surface and simultaneously forming an antimicrobial film on said surface, comprising:

1) providing a liquid water solution of an antimicrobial nitrogen-containing polysaccharide;

2) heating said liquid water solution to convert said liquid water solution to a water vapor having a temperature of 275° F. to 310° F.;

3) exposing said surface to said water vapor, thereby sanitizing or disinfecting said surface with heat from said water vapor; and 4) simultaneously depositing said antimicrobial nitrogen containing polysaccharide from said water vapor onto said surface, thereby forming said antimicrobial film of said nitrogen containing polysaccharide on said surface.

6. The method of claim 5 wherein said antimicrobial nitrogen-containing polysaccharide is a chitin derivative or chitosan or carboxymethylated chitosan.

7. The method of claim 6 wherein said water vapor is steam or dry vapor steam, forming a composition of steam and chitosan.

8. The method of claim 7, further comprising applying said steam or said dry vapor steam to said surface for 1 to 20 seconds and at a distance of 1 to 20 inches, wherein no said liquid water solution is applied to said surface.

* * * * *

UNITED STATES PATENT AND TRADEMARK OFFICE
CERTIFICATE OF CORRECTION

PATENT NO. : 9,149,036 B1  
APPLICATION NO. : 14/195697  
DATED : October 6, 2015  
INVENTOR(S) : Lloyd Starks and Stanley R. Weller Page 1 of 1

It is certified that error appears in the above-identified patent and that said Letters Patent is hereby corrected as shown below:

On the title page

Item (71) Applicants, change the listing of Applicants from "Lloyd Starks, Chattanooga, TN (US)" to read -- Lloyd Starks, Chattanooga, TN (US); Stanley R. Weller, Marietta, GA (US) --.

Item (75) Inventors, change the listing of Inventors from "Lloyd Starks, Chattanooga, TN (US)" to read -- Lloyd Starks, Chattanooga, TN (US); Stanley R. Weller, Marietta, GA (US) --.

Signed and Sealed this
Eighth Day of March, 2016

Michelle K. Lee
*Director of the United States Patent and Trademark Office*